(12) United States Patent
Wang et al.

(10) Patent No.: US 8,017,777 B2
(45) Date of Patent: Sep. 13, 2011

(54) PROCESS FOR THE PREPARATION OF BUPRENORPHINE AND DERIVATIVES FOR BUPRENORPHINE

(75) Inventors: Peter X. Wang, Clarkson Valley, MO (US); Tao Jiang, St. Louis, MO (US); Gary L. Cantrell, Troy, IL (US); David W. Berberich, St. Peters, MO (US); Bobby N. Trawick, Florissant, MO (US); Subo Liao, Ballwin, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 537 days.

(21) Appl. No.: 12/316,861

(22) Filed: Dec. 17, 2008

(65) Prior Publication Data

US 2009/0156817 A1    Jun. 18, 2009

Related U.S. Application Data

(60) Provisional application No. 61/014,090, filed on Dec. 17, 2007.

(51) Int. Cl.
*C07D 489/12* (2006.01)
*C07D 489/02* (2006.01)

(52) U.S. Cl. ............................................. 546/39; 546/45
(58) Field of Classification Search ................... 546/39, 546/45
See application file for complete search history.

(56) References Cited

U.S. PATENT DOCUMENTS

2008/0312441 A1    12/2008   Mannino et al.

OTHER PUBLICATIONS

Marton et al., Herstellung von 6,14-Ethenomorphinan-Derivaten, Liebigs Ann. Chem., 1993, pp. 915-919, XP 002519987.
Rapoport et al., "The Synthesis of Thebaine and Northebaine from Codeinone Dimethyl Ketal", J. Am. Chem. Soc., Apr. 12, 1967, 89:8; pp. 1942-1947, XP 002519988.
Nagase et al., "The Facility of Formation of a $\Delta^6$ Bond in Dihydromorphinone and Related Opiates", Am. Chem. Soc., 1989, 54, pp. 4120-4125, XP 002519990.
Bartels-Keith, "Syntheses Related to Northebaine. Part 1. Northebaine and N-Allyl-northebaine", J. Chem. Soc., 1966, pp. 617-624, XP 009114187.

*Primary Examiner* — Charanjit Aulakh

(57) ABSTRACT

The invention generally provides processes for the production of buprenophine and derivatives of buprenorphine. In particular, the process may encompass synthetic routes for the production of buprenorphine or derivatives of buprenorphine from norhydromorphone or derivatives of norhydromorphone.

22 Claims, No Drawings

PROCESS FOR THE PREPARATION OF BUPRENORPHINE AND DERIVATIVES FOR BUPRENORPHINE

CROSS-REFERENCE TO RELATED APPLICATION

This application claims priority from Provisional Application Ser. No. 61/014,090 filed on Dec. 17, 2007, which is hereby incorporated by reference in its entirety.

FIELD OF THE INVENTION

The present invention generally relates to processes for the production of buprenophine and derivatives of buprenorphine.

BACKGROUND OF THE INVENTION

Opiate compounds such as (−)-naltrexone, (−)-naloxone, (−)-nalbuphene, (−)-nalmefene, and (−)-buprenorphine have been used for addiction therapy. (−)-Buprenorphine, in particular, is increasingly being used for the treatment of heroin addiction. Recently, the (+)-opiate enantiomers have been shown to have important bioactivities that differ from their (−) counter parts. Because of the exceptional opiate medicinal activity of (−)-buprenorphine, there is great interest in the therapeutic efficacy of (+)-buprenorphine. In order to explore the possible benefits of this compound, there is a need in the art for synthetic routes to produce (+)-buprenorphine or its derivatives in an efficient and cost effective manner that generates a high yield of product having a high degree of purity.

SUMMARY OF THE INVENTION

The invention generally provides processes for the production of buprenophine and derivatives of buprenorphine. In one exemplary iteration, for example, the process may encompass synthetic routes for the production of buprenorphine or derivatives of buprenorphine from norhydromorphone or derivatives of norhydromorphone in accordance with the following reaction scheme:

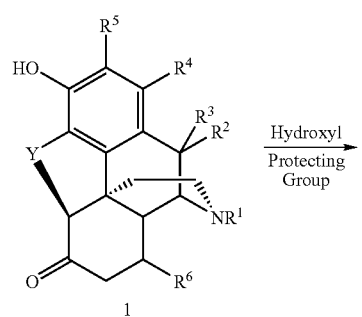

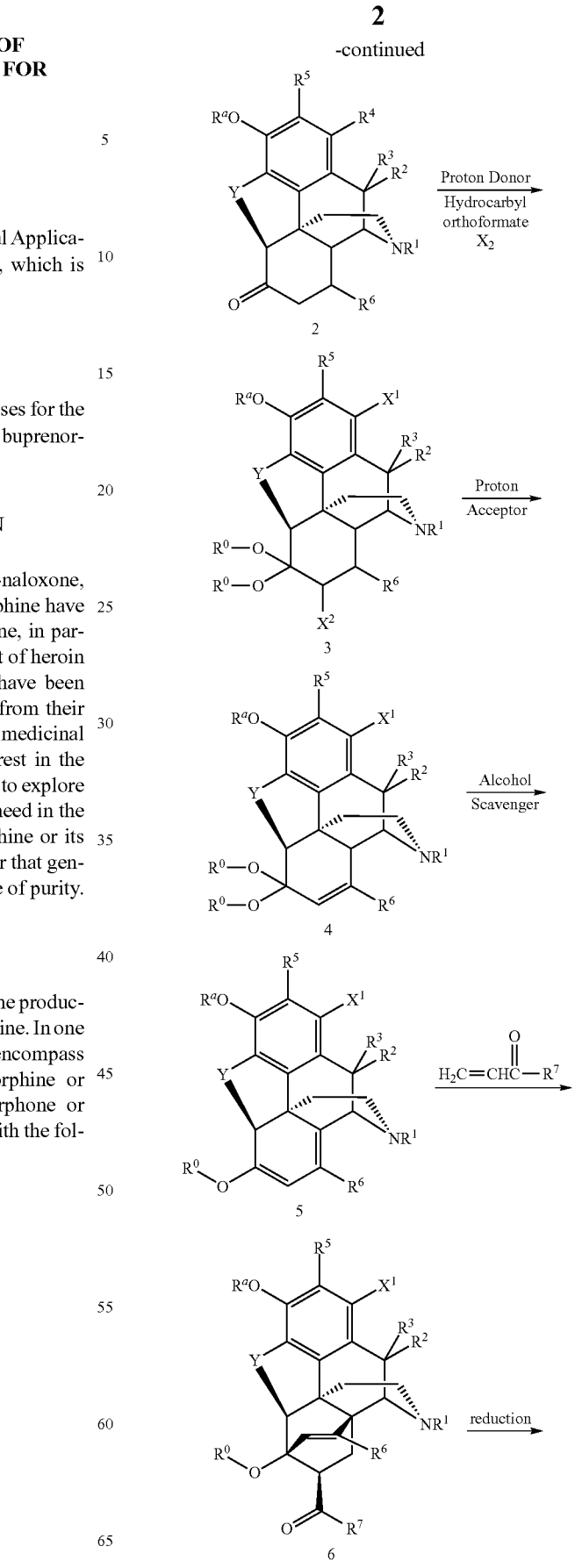

-continued

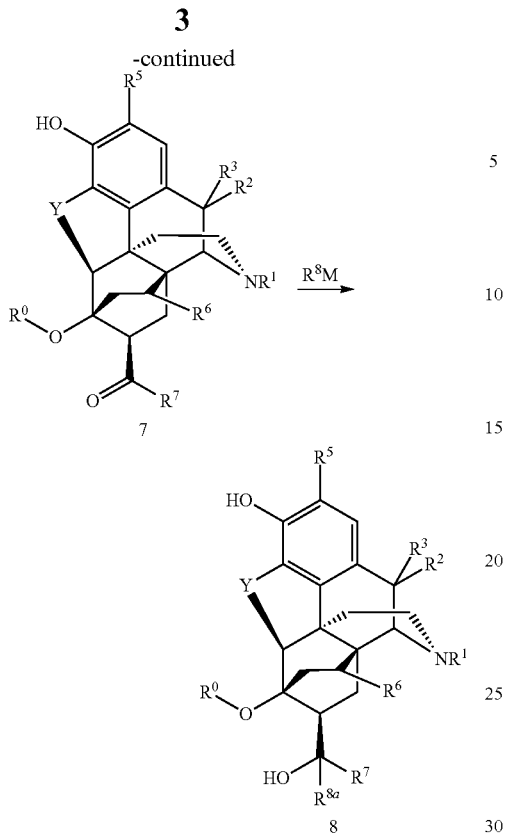

wherein:
- $R^0$ and $R^8$ are independently selected from the group consisting of hydrocarbyl, and substituted hydrocarbyl;
- $R^1$, $R^7$ and $R^{8a}$ are independently selected from the group consisting of hydrogen, hydrocarbyl, and substituted hydrocarbyl;
- $R^2$, $R^3$, $R^4$, $R^5$, and $R^6$ are independently selected from the group consisting of hydrogen, halogen, $OR^b$, hydrocarbyl, and substituted hydrocarbyl, or $R^2$ and $R^3$ may together form $\{-\}=O$;
- $R^a$ is a hydroxyl protecting group;
- $R^b$ is selected from the group consisting of hydrogen, hydrocarbyl, and substituted hydrocarbyl;
- M is selected from Group IA metal salts, and Group IIA metal salts;
- X, and $X^2$ are independently selected from the group consisting of bromide, and chloride;
- $X^1$ is bromide or chloride when $R^4$ is hydrogen, and $X^1$ is $R^4$ when $R^4$ is not hydrogen; and
- Y is selected from the group consisting of oxygen, sulfur, and nitrogen.

Other aspects and iterations of the invention are described in more detail below.

DETAILED DESCRIPTION OF THE INVENTION

The present invention provides processes and intermediate compounds for producing buprenorphine. In particular, the process encompasses synthetic routes for the production of buprenorphine or derivatives of buprenorphine from norhydromorphone or derivatives of norhydromorphone. While it is envisioned that the synthetic routes described herein may be utilized to produce (±)-buprenorphine, in an exemplary aspect of the invention, the process encompasses the production of (+)-buprenorphine or derivatives of (+)-buprenorphine.

For purposes of illustration, Reaction Scheme 1 depicts the production of compound 8 from compound 1 in accordance with one aspect of the present invention:

Reaction Scheme 1:

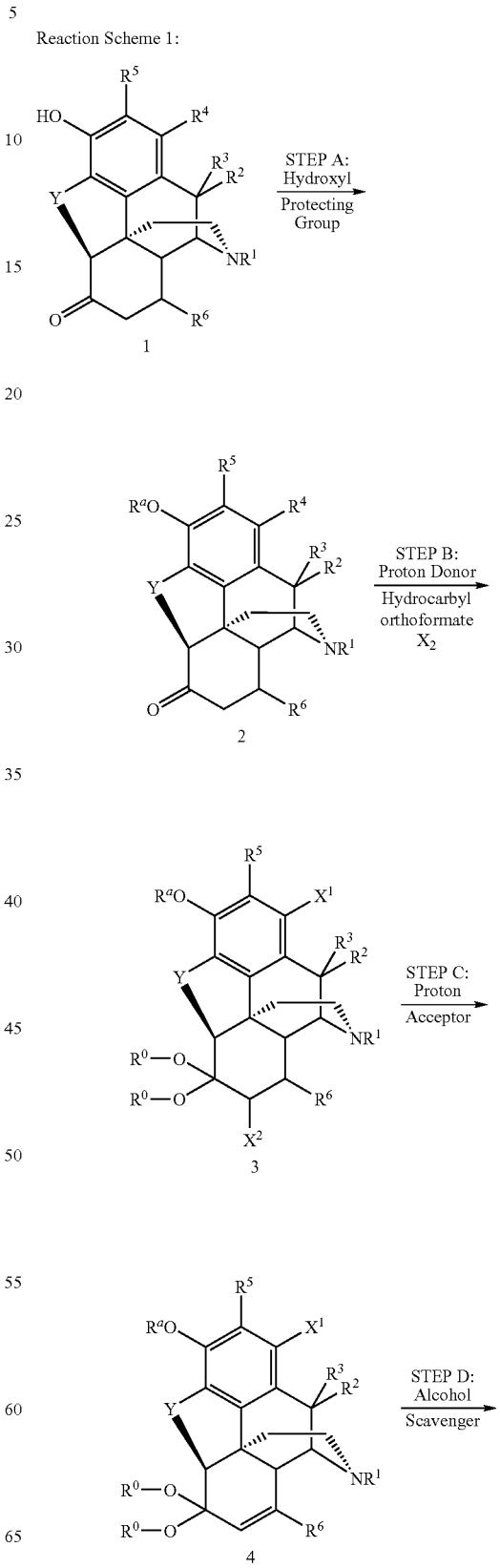

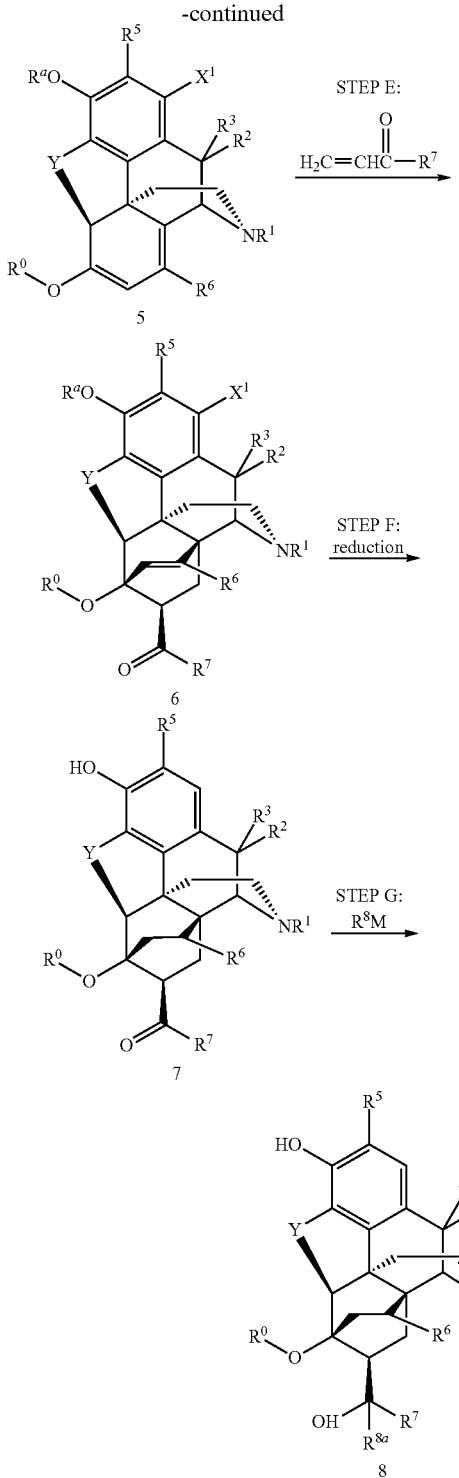

$R^a$ is an oxygen protecting group;
$R^b$ is selected from the group consisting of hydrogen, hydrocarbyl, and substituted hydrocarbyl;
M is selected from Group IA metal salts, and Group IIA metal salts;
X, and $X^2$ are independently selected from the group consisting of bromide, and chloride;
$X^1$ is bromide or chloride when $R^4$ is hydrogen, and $X^1$ is $R^4$ when $R^4$ is not hydrogen; and
Y is selected from the group consisting of oxygen, sulfur, and nitrogen.

In an exemplary embodiment, $R^1$, $R^7$ and $R^{8a}$ are independently selected from the group consisting of hydrogen, alkyl, substituted alkyl, alkenyl, substituted alkenyl, aryl, and substituted aryl; M is selected from the group consisting of NaR, LiR, or $RMgX^3$, where $X^3$ is chloride or bromide and R is a hydrocarbyl or substituted hydrocarbyl; X, $X^1$, and $X^2$ are each bromide; and Y is oxygen. Included among some of the more preferred hydrocarbyl groups for $R^1$, $R^7$ and $R^{8a}$ are methyl, ethyl, propyl, isopropyl, butyl, isobutyl, tertiary butyl, pentyl, cyclopropyl, cyclobutyl, cyclopentyl, cyclohexyl, phenyl, methylphenyl, or benzyl. In an exemplary embodiment, $R^1$ is {–}$CH_2$-cyclopropyl; $R^7$ is methyl, and $R^8$ is tertiary butyl.

For ease of discussion, the ring atoms of the core morphinan structure referenced herein are numbered as follows:

As illustrated in the core morphinan structure, there are four chiral carbons comprising any of the compounds utilized in the process of the invention, i.e., carbons 5, 13, 14, and 9. Thus, the configuration of compounds of the invention may be RRRR, RRRS, RRSR, RSSS, SRRR, SRRS, SRSR, SRSS, RSRR, RSRS, RSSR, RSSS, SSRR, SSRS, SSSR, or SSSS, with respect to C5, to C13, C14, and C9, provided that the C15 and the C16 atoms are both either on the alpha face of the molecule or the beta face of the molecule.

(a) Step A: Conversion of Compound 1 to Compound 2

Generally, the substrate for preparation of compound 2 corresponds to compound 1 depicted in Reaction Scheme 1. An exemplary compound 1 comprises the following substituents: $R^1$ is {$CH_2$}-cyclopropyl; $R^2$, $R^3$, $R^4$, $R^5$, and $R^6$ are each hydrogen, and Y is oxygen. For this exemplary embodiment, compound 1 may be prepared by reacting (+)-norhydromorphone with cyclopropyl-$CH_2Br$. Alternatively, compound 1 may be prepared by the reductive amination of (+)-norhydromorphone with cyclopropyl-CHO.

In Step A of the process, compound 1 is contacted with a protecting group to protect the hydroxyl group at position C(3). Suitable hydroxyl protecting groups include ethers (e.g., allyl, triphenylmethyl (trityl or Tr), benzyl, p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsiwherein:
$R^0$ and $R^8$ are independently selected from the group consisting of hydrocarbyl, and substituted hydrocarbyl;
$R^1$, $R^7$ and $R^{8a}$ are independently selected from the group consisting of hydrogen, hydrocarbyl, and substituted hydrocarbyl;
$R^2$, $R^3$, $R^4$, $R^5$, and $R^6$ are independently selected from the group consisting of hydrogen, halogen, $OR^b$, hydrocarbyl, and substituted hydrocarbyl, or $R^2$ and $R^3$ may together form {–}=O;

lylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups for the hydroxy group and the synthesis thereof may be found in "Protective Groups in Organic Synthesis" by T. W. Greene and P. G. M. Wuts, John Wiley & Sons, 1999. In an exemplary embodiment, the hydroxyl protecting group comprises aryl-$CH_2Br$.

The molar ratio of compound 1 to hydroxyl protecting group is typically from about 1:1 to about 1:3. In an exemplary embodiment, the molar ratio of compound 1 to hydroxyl protecting group is from about 1:1 to about 1:1.5.

The solvent system used in Step A of the process may comprise an organic solvent, protic solvent, aprotic solvent, and combinations of each of these. Representative organic solvents include, but are not limited to, alkane and substituted alkane solvents (including cycloalkanes), aromatic hydrocarbons, esters, ethers, ketones, combinations thereof, and the like. Specific organic solvents that may be employed, include, for example, acetonitrile, benzene, butyl acetate, t-butyl methylether, t-butyl methylketone, chlorobenzene, chloroform, chloromethane, cyclohexane, dichloromethane, dichloroethane, diethyl ether, ethyl acetate, fluorobenzene, heptane, hexanes, isobutylmethylketone, isopropyl acetate, methylethylketone, methyltetrahydrofuran, pentyl acetate, n-propyl acetate, tetrahydrofuran, toluene, combinations thereof, and the like.

When present, the protic solvent may be water, an alcohol, $RCO_2H$ (wherein R is hydrogen or an alkyl), a water/alcohol mixture, or a water/water-miscible solvent mixture. Representative alcohols for the water/alcohol mixture include, for example, methanol, ethanol, isopropyl alcohol, isobutyl alcohol, t-butyl alcohol, n-propyl alcohol, n-butyl alcohol, and combinations thereof. Other water-miscible solvents for the water/water-miscible solvent mixture include, for example, acetonitrile, N,N-dimethylformamide, 1-methyl-2-pyrrolidinone, N,N-dimethylacetamide, acetone, tetrahydrofuran, and combinations thereof.

Non-limiting examples of aprotic solvents include ether solvents, acetone, acetonitrile, benzene, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), N,N-dimethylacetamide (DMAC), N-methylpyrrolidinone (NMP), ethyl acetate, ethyl formate, ethyl methyl ketone, formamide, hexamethylphosphoramide, methyl acetate, N-methylacetamide, N-methylformamide, methylene chloride, nitrobenzene, nitromethane, propionitrile, sulfolane, tetramethylurea, tetrahydrofuran (THF), toluene, trichloromethane. In a preferred embodiment, the aprotic solvent may be dimethylformamide, dimethyl sulfoxide, dioxane, formamide, or N-methylacetamide.

The weight ratio of solvent(s) to compound 1 may range from about 1:1 to about 20:1. In one embodiment, the weight ratio of solvent(s) to compound 1 may range from about 1:1 to about 3:1. In another embodiment, the weight ratio of solvent(s) to compound 1 may range from about 6:1 to about 12:1. In still another embodiment, the weight ratio of solvent(s) to compound 1 may range from about 12:1 to about 20:1. In a preferred embodiment, the weight ratio of solvent(s) to compound 1 may range from about 3:1 to about 6:1.

To form the reaction mixture, compound 1 is typically combined with the solvent(s) prior to the addition of the hydroxyl protecting group. Alternatively, however, the solvent(s), and the hydroxyl protecting group may be combined, and thereafter added to the reaction vessel containing compound 1.

The temperature of the reaction mixture for Step A of the process will typically be within the range of about 0° C. to about 65° C. More typically, the reaction will be carried out at a temperature between about 25° C. and about 50° C. The reaction is preferably performed under ambient pressure, and preferably in an inert atmosphere (e.g., nitrogen or argon).

(b) Step B: Conversion of Compound 2 to Compound 3

The substrate for preparation of compound 3 corresponds to compound 2 depicted in Reaction Scheme 1. An exemplary compound 2 comprises the following substituents: $R^a$ is aryl-$CH_2$; $R^1$ is $\{CH_2\}$-cyclopropyl; $R^2$, $R^3$, $R^4$, $R^5$, and $R^6$ are each hydrogen, and Y is oxygen.

In Step B of the process, compound 2 is contacted with a trihydrocarbyl orthoformate. The hydrocarbyl may be alkyl, substituted alkyl, alkenyl, substituted alkenyl, aryl, and substituted aryl. In one alternative of this embodiment, the hydrocarbyl is selected from the group consisting of methyl, ethyl, propyl, isopropyl, butyl, isobutyl, tertiary butyl, pentyl, cyclopropyl, cyclobutyl, cyclopentyl, cyclohexyl, phenyl, methylphenyl, and benzyl. In an exemplary embodiment, the hydrocarbyl is trimethyl orthoformate or triethyl orthoformate.

To facilitate the reaction of compound 2 with the trihydrocarbyl orthoformate, the reaction is generally carried out in the presence of a proton donor. The proton donor generally has a PKa less than about 0. Suitable proton donors having this characteristic include, but are not limited to $MeSO_3H$, poly $H_3PO_4$, $H_3PO_4$, $H_2SO_4$, HCl, HBr, $HClO_4$, HI, $HNO_3$, $CF_3SO_3H$, p-methyltoluenesulfonic acid, $HClO_3$, $HBrO_4$, $HIO_3$, and $HIO_4$.

The molar ratio of compound 2 to trihydrocarbyl orthoformate to proton donor is typically from about 1:1:1.5 to about 1:3:6. In an exemplary embodiment, the molar ratio of compound 2 to trihydrocarbyl orthoformate to proton donor is typically from about 1:1:1.5 to about 1:2:3.

In order to form the reaction mixture, compound 2 and the trihydrocarbyl orthoformate are typically combined with an aprotic solvent prior to the addition of the proton donor. Suitable aprotic solvents are as described in Step A. In an exemplary embodiment, the reaction is conducted in the presence of an alcohol-containing solvent. Suitable alcohol-containing solvents include methanol, ethanol, isopropyl alcohol, isobutyl alcohol, t-butyl alcohol, n-propyl alcohol, n-butyl alcohol, and combinations thereof. After these reactants have been combined, a halogen selected from chloride and bromide is added to the reaction mixture. The halogen is added in an amount from about 2 to about 2.5 equivalents per equivalent of compound 2.

The temperature of the reaction mixture for Step B of the process will typically be within the range of about 20° C. to about 120° C. More typically, the reaction will be carried out at a temperature between about 45° C. and about 80° C. The reaction is preferably performed under ambient pressure, and preferably in an inert atmosphere (e.g., nitrogen or argon).

The reaction may be quenched by contacting the reaction mixture with a proton acceptor. In general, the proton acceptor has a pKa of between about 7 and about 13, preferably between about 8 and about 10. Representative proton acceptors that may be employed include, but are not limited to, borate salts (such as, for example, $NaBO_3$), di- and tri-basic phosphate salts (such as, for example, $Na_2HPO_4$ and $Na_3PO_4$), bicarbonate salts (such as, for example, $NaHCO_3$, $KHCO_3$, mixtures thereof, and the like), hydroxide salts (such as, for example, NaOH, KOH, mixtures thereof, and the like), carbonate salts (such as, for example, $Na_2CO_3$, $K_2CO_3$, mixtures thereof, and the like), organic bases (such as, for example, pyridine, triethylamine, diisopropylethylamine, N-methylmorpholine, N,N'-dimethylaminopyridine, and mixtures thereof), organic buffers (such as, for example, N-(2-acetamido)-2-aminoethane sulfonic acid (ACES), N-(2-acetamido)-iminodiacetic acid (ADA), N,N-bis(2-hydroxyethyl)glycine (BICINE), 3-(cyclohexylamino)-1-propanesulfonic acid (CAPS), 2-(cyclohexylamino)ethanesulfonic acid (CHES), 4-(2-hydroxyethyl)-1-piperazinepropanesulfonic acid (EPPS), 4-(2-hydroxyethyl)piperazine-1-ethanesulfonic acid (HEPES), 2-(4-morpholinyl)ethanesulfonic acid (MES), 4-morpholinepropanesulfonic acid (MOPS), 1,4-piperazinediethanesulfonic acid (PIPES), [(2-hydroxy-1,1-bis(hydroxymethyl)ethyl)amino]-1-propanesulfonic acid (TAPS), 2-[(2-hydroxy-1,1-bis(hydroxymethyl)ethyl)amino]ethanesulfonic acid (TES), salts and/or mixtures thereof, and the like), and combinations thereof. Where the proton acceptor is an organic buffer, the organic buffer preferably lacks a hydroxy-substituted nitrogen atom, as this substituent may compete for reaction with the haloformate reactant. In a preferred embodiment, the proton acceptor is selected from hydroxide salts such as NaOH, KOH, and LiOH.

(c) Step C: Conversion of Compound 3 to Compound 4

The substrate for preparation of compound 4 corresponds to compound 3 depicted in Reaction Scheme 1. An exemplary compound 3 comprises the following substituents: $R^0$ is methyl; $R^a$ is aryl-$CH_2$; $R^1$ is {$CH2$}-cyclopropyl; $R^2$, $R^3$, $R^5$, and $R^6$ are each hydrogen; $X^1$ and $X^2$ are each bromide; and Y is oxygen.

In Step C of the process, compound 3 is contacted with a proton acceptor. In general, the proton acceptor has a p$K_b$ less than 0. Representative proton acceptors that may be employed include, but are not limited to, LiOH, NaOH, KOH, LiOR, NaOR, KOR, $LiNR_2$, $NaNR_2$, and $KNR_2$, wherein R is an alkyl group.

To enable the reaction to proceed at a commercially desirable rate, the molar ratio of compound 3 to proton acceptor is typically from about 1:1 to about 1:10. In an exemplary embodiment, the molar ratio of compound 3 to proton acceptor is typically from about 1:2 to about 1:6.

To form the reaction mixture, compound 3 is typically combined with an aprotic solvent prior to the addition of the proton acceptor. Alternatively, however, the aprotic solvent, and the proton acceptor may be combined, and thereafter added to the reaction vessel containing compound 3. Suitable aprotic solvents are as described for Step A of the process.

The temperature of the reaction mixture for Step C of the process will typically be within the range of about 40° C. to about 120° C. More typically, the reaction will be carried out at a temperature between about 65° C. and about 80° C. The reaction is preferably performed under ambient pressure, and preferably in an inert atmosphere (e.g., nitrogen or argon).

(d) Step D: Conversion of Compound 4 to Compound 5

The substrate for preparation of compound 5 corresponds to compound 4 depicted in Reaction Scheme 1. An exemplary compound 4 comprises the following substituents: $R^0$ is methyl; $R^a$ is aryl-$CH_2$; $R^1$ is {$CH_2$}-cyclopropyl, {$CH_2$}-cyclobutyl, {–}alkyl; $R^2$, $R^3$, $R^5$, and $R^6$ are each hydrogen, $X^1$ is bromide; and Y is oxygen.

In Step D of the process, compound 4 is contacted with an alcohol scavenger. The alcohol may be an alcohol having from about 1 to about 8 carbon atoms. In an exemplary embodiment, the alcohol scavenger is a methanol scavenger. Suitable methanol scavengers include $P_2O_5$, $POCl_3$, $POBr_3$, $PCl_3$, $PBr_3$, $SOCl_2$, $SOBr_2$, $MeSO_2Cl$, $(MeSO_2)_2O$, $SO_3$, $(CF_3SO_2)_2O$, $(CF_3CO)_2O$, $(CR_3CO)_2O$, and $R_3SiX$ (wherein X is Cl or Br, and R is an alkyl group).

The molar ratio of compound 4 to alcohol scavenger is typically from about 1:0.3 to about 1:3. In an exemplary embodiment, the molar ratio of compound 4 to alcohol scavenger is typically from about 1:0.5 to about 1:1.5. The reaction is generally conducted in the presence of an aprotic solvent. Suitable aprotic solvents are as described above for Step A of the process.

The temperature of the reaction mixture for Step D of the process will typically be within the range of about 0° C. to about 120° C. More typically, the reaction will be carried out at a temperature between about 20° C. and about 80° C. The reaction is preferably performed under ambient pressure, and preferably in an inert atmosphere (e.g., nitrogen or argon).

(e) Step E: Conversion of Compound 5 to Compound 6

The substrate for preparation of compound 6 corresponds to compound 5 depicted in Reaction Scheme 1. An exemplary compound 5 comprises the following substituents: $R^0$ is methyl; $R^a$ is aryl-$CH_2$; $R^1$ is {$CH_2$}-cyclopropyl; $R^2$, $R^3$, $R^5$, and $R^6$ are each hydrogen, $X^1$ is bromide; and Y is oxygen.

In Step E of the process, compound 5 is contacted with a vinyl ketone. In an exemplary embodiment the vinyl ketone corresponds to the following formula:

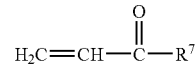

wherein $R^7$ is a hydrocarbyl or a substituted hydrocarbyl. Suitable hydrocarbyl groups include alkyl, substituted alkyl, alkenyl, substituted alkenyl, aryl, and substituted aryl. More preferred hydrocarbyls include methyl, ethyl, propyl, isopropyl, butyl, isobutyl, tertiary butyl, pentyl, cyclopropyl, cyclobutyl, cyclopentyl, cyclohexyl, phenyl, methylphenyl, or benzyl. In an exemplary embodiment, the hydrocarbyl is methyl.

The molar ratio of compound 5 to vinyl ketone is typically from about 1:1 to about 1:10. In an exemplary embodiment, the molar ratio of compound 4 to vinyl ketone is typically from about 1:1 to about 1:3. The reaction is generally conducted in the presence of an organic solvent. Suitable organic solvents are as described above for Step A of the process.

The temperature of the reaction mixture for Step E of the process will typically be within the range of about 20° C. to about 120° C. More typically, the reaction will be carried out at a temperature between about 80° C. and about 120° C. The reaction may be performed under either ambient pressure or under higher pressure (in order to increase the reaction temperature) and preferably in an inert atmosphere (e.g., nitrogen or argon).

(f) Step F.: Conversion of Compound 6 to Compound 7

The substrate for preparation of compound 7 corresponds to compound 6 depicted in Reaction Scheme 1. An exemplary compound 6 comprises the following substituents: $R^0$ is methyl; $R^a$ is aryl-$CH_2$; $R^1$ is {$CH_2$}-cyclopropyl, {$CH_2$}-cyclobutyl, {–}-alkyl; $R^2$, $R^3$, $R^5$, and $R^6$ are each hydrogen, $R^7$ is methyl; $X^1$ is bromide; and Y is oxygen.

In Step F of the process, compound 6 is reduced to form compound 7. Generally, the reduction is carried out to reduce the unsaturation between the vinyl carbon groups. Additional treatment of compound 6 with a hydrolyzing agent may be performed to remove the hydroxy protecting group, $R^a$.

A wide variety of reducing approaches may be employed in Step F including, for example, chemical reduction, catalytic reduction, and the like. Representative reducing agents for use in catalytic reduction methods with hydrogen include commonly used catalysts such as, for example, platinum catalysts (e.g., platinum black, colloidal platinum, platinum oxide, platinum plate, platinum sponge, platinum wire, and the like), palladium catalysts (e.g., palladium black, palladium on barium carbonate, palladium on barium sulfate, colloidal palladium, palladium on carbon, palladium hydroxide on carbon, palladium oxide, palladium sponge, and the like), nickel catalysts (e.g., nickel oxide, Raney nickel, reduced nickel, and the like), cobalt catalysts (e.g., Raney cobalt, reduced cobalt, and the like), iron catalysts (e.g., Raney iron, reduced iron, Ullmann iron, and the like), and others. In an exemplary embodiment, compound 6 is reduced using catalytic reduction (e.g., Pd/C catalyzed transfer hydrogenation). Preferred catalysts include transition metal catalysts selected from the group consisting of Pd/C, PVC, Ru/C, and Rh/C.

The molar ratio of compound 6 to transition metal catalyst is typically from about 1:0.0005 to about 1:0.05. In an exemplary embodiment, the molar ratio of compound 6 to transition metal catalyst is typically from about 1:0.008 to about 1:0.001. The reaction is generally conducted in the presence of an aprotic solvent. Suitable aprotic solvents are as described above for Step A of the process.

The temperature of the reaction mixture for Step F of the process will typically be within the range of about 60° C. to about 120° C. More typically, the reaction will be carried out at a temperature between about 80° C. and about 110° C. The reaction is preferably performed under pressurized hydrogen. Generally, the hydrogen pressure is between about 0 and about 500 psi, and more preferably, between about 30 and about 120 psi.

g) Step G: Conversion of Compound 7 to Compound 8

The substrate for preparation of compound 8 corresponds to compound 7 depicted in Reaction Scheme 1. An exemplary compound 7 comprises the following substituents: $R^0$ is methyl; $R^1$ is {$CH_2$}-cyclopropyl; $R^2$, $R^3$, $R^5$, and $R^6$ are each hydrogen, $R^7$ is methyl; and Y is oxygen.

In Step G of the process, compound 7 is contacted with $R^8M$; wherein $R^8$ is selected from a hydrocarbyl, and substituted hydrocarbyl; and M is selected from Group IA metal salts, and Group IIA metal salts. The hydrocarbyl or substituted hydrocarbyl forming $R^8$ may preferably be alkyl, substituted alkyl, alkenyl, substituted alkenyl, aryl, and substituted aryl. In an exemplary embodiment $R^8$ is methyl, ethyl, propyl, isopropyl, butyl, isobutyl, tertiary butyl, pentyl, cyclopropyl, cyclobutyl, cyclopentyl, cyclohexyl, phenyl, methylphenyl, or benzyl. An exemplary M is selected from the group consisting of NaR, LiR, or $RMgX^3$, where $X^3$ is chloride or bromide and R is a hydrocarbyl or substituted hydrocarbyl. In another exemplary embodiment, $R^8M$ comprises tertiary butyl MgCl.

The molar ratio of compound 7 to $R^8M$ is typically from about 1:2 to about 1:10. In an exemplary embodiment, the molar ratio of compound 7 to $R^8M$ is typically from about 1:3 to about 1:8. The reaction is generally conducted in the presence of an aprotic solvent. Suitable aprotic solvents are as described above for Step A of the process.

The temperature of the reaction mixture for Step G of the process will typically be within the range of about 60° C. to about 120° C. More typically, the reaction will be carried out at a temperature between about 80° C. and about 110° C. The reaction is preferably performed under ambient pressure, and preferably in an inert atmosphere (e.g., nitrogen or argon).

The product formed by Step G, compound 8, may have the following substituents:

$R^0$ is methyl;

$R^1$, $R^7$ and $R^{8a}$ are independently selected from the group consisting of hydrogen, hydrocarbyl, and substituted hydrocarbyl;

$R^2$, $R^3$, $R^5$, and $R^6$ are independently selected from the group consisting of hydrogen, halogen, {—}=O, $OR^b$, hydrocarbyl, and substituted hydrocarbyl;

$R^b$ is selected from the group consisting of hydrogen, hydrocarbyl, and substituted hydrocarbyl; and Y is selected from the group consisting of oxygen, and nitrogen.

In an exemplary embodiment, $R^1$, $R^7$ and $R^{8a}$ are independently selected from the group consisting of hydrogen, alkyl, substituted alkyl, alkenyl, substituted alkenyl, aryl, and substituted aryl; and Y is oxygen. Included among some of the more preferred hydrocarbyl groups for $R^1$, $R^7$ and $R^{8a}$ are methyl, ethyl, propyl, isopropyl, butyl, isobutyl, tertiary butyl, pentyl, cyclopropyl, cyclobutyl, cyclopentyl, cyclohexyl, phenyl, methylphenyl, or benzyl. In an exemplary embodiment, compound 8 comprises (+)-buprenorphine or a salt or a derivative of (+)-buprenorphine having the following formula:

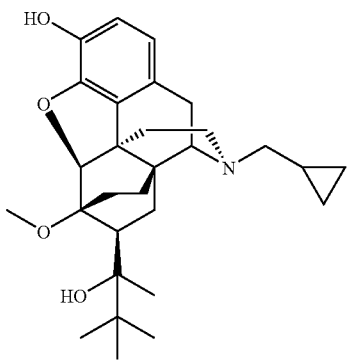

8

As will be appreciated by a skilled artisan, the yield and purity of compound 8 produced by the process can and will vary depending upon the particular reactants and reaction parameters selected. The yield will generally range from about 50% to greater than about 90% for step G. More typically, the yield will range from about 60% to greater than about 80%. For the overall reaction, i.e. from compound 1 to compound 8, the yield will generally range from about 8% to greater than about 20%. The purity will generally range from about 90% to greater than about 99% as determined by chromatography (e.g., HPLC), more typically, the purity will be greater than about 98%.

In certain embodiments where $R^{8a}$ is hydrogen, the reaction may proceed via ketone reduction in the presence of $M^1BH_{(4-a)}R_a$, $M^1AlR_aH_{(4-a)}$, $BH_bR_{(3-b)}$ or $AlR_bR_{(3-b)}$, wherein $M^1$ is K, Na, or Li; R is an alkyl, aryl, alkoxy or R'C(O)O; a is 1, 2, or 3; and b is 1 or 2.

Definitions

The term "acyl," as used herein alone or as part of another group, denotes the moiety formed by removal of the hydroxy group from the group COOH of an organic carboxylic acid, e.g., RC(O)—, wherein R is $R_1$, $R_1O$—, $R_1R_2N$—, or $R_1S$—, $R_1$ is hydrocarbyl, heterosubstituted hydrocarbyl, or heterocyclo, and $R_2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alcohol scavenger" as used herein is a reagent that can react with an alcohol and release an acid at the same time.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkaryl" or "alkylaryl" as used herein describes groups which are preferably aryl groups having a lower alkyl substituent, such as toluyl, ethylphenyl, or methylnapthyl.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aralkyl" as used herein describes groups which are preferably lower alkyl containing from one to eight carbon atoms having an aryl substituent, such as benzyl, phenylethyl, or 2-napthylmethyl.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

The terms "hydroxy protecting group" as used herein denote a group capable of protecting a free hydroxy group ("protected hydroxy"), which, subsequent to the reaction for which protection is employed, may be removed without disturbing the remainder of the molecule.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above compounds, products and methods without departing from the scope of the invention, it is intended that all matter contained in the above description and in the examples given below, shall be interpreted as illustrative and not in a limiting sense.

EXAMPLES

The following examples describe various iterations of the invention.

Example 1

Production of (+)-buprenorphine from (+)-norhydromorphone

Reaction Scheme 2 depicts the production of (+)-buprenorphine from (+)-norhydromorphone according to one aspect of the invention:

Reaction Scheme 2:

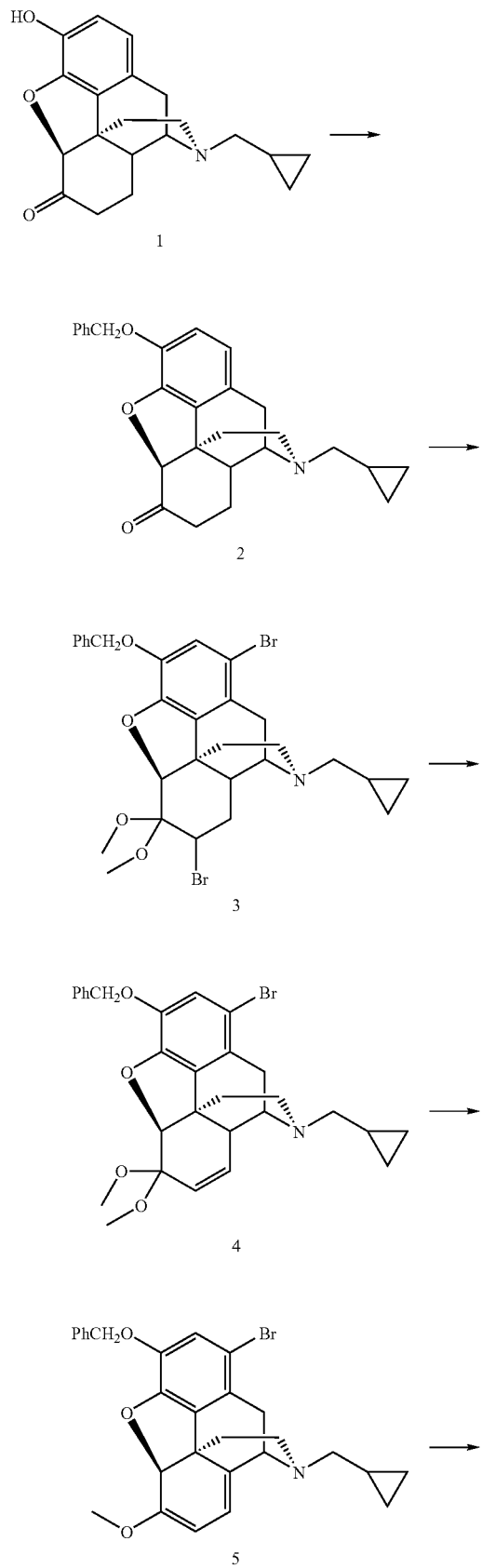
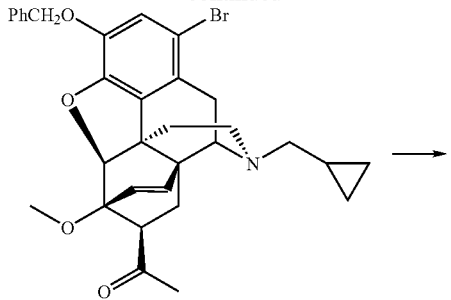
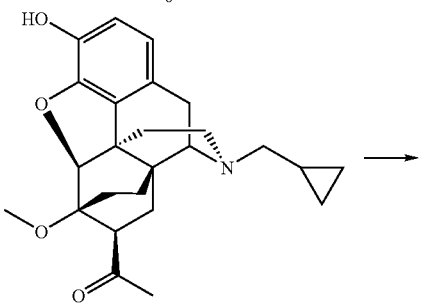
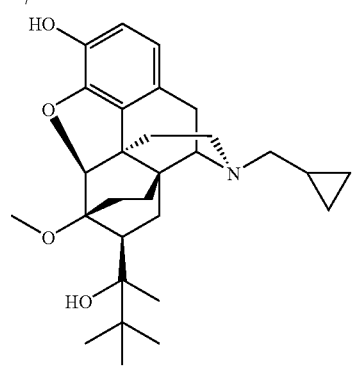

(+)-Norhydromorphone may be converted to compound 1 by reacting it with cyclopropyl-CH₂Br. Alternatively, compound 1 may be formed by the reductive amination of (+)-norhydromorphone with cyclopropyl-CHO. Compound 1 may be contacted with benzylCH₂Br to form compound 2. Compound 2 may be heated under reflux in methanol in the presence of a proton donor and trimethyl orthoformate and two equivalents of bromine to form compound 3. Compound 3 may be heated in DMSO in the presence of a proton acceptor, such as KOH, to produce compound 4. Compound 4 may be combined with a methanol scavenger to produce compound 5. Compound 5 may be contacted with methyl vinyl ketone to from compound 6. Compound 6 may converted to compound 7 under pressurized hydrogen in the presence of Pd on carbon. The reaction of compound 7 with tertiary butylMgCl produces compound 8, (+)-buprenorphine.

Example 2

Production of (+)-buprenorphine from (+)-norhydromorphone

Reaction Scheme 2a depicts the production of (+)-buprenorphine from (+)-norhydromorphone according to another of the invention:

Reaction Scheme 2a:

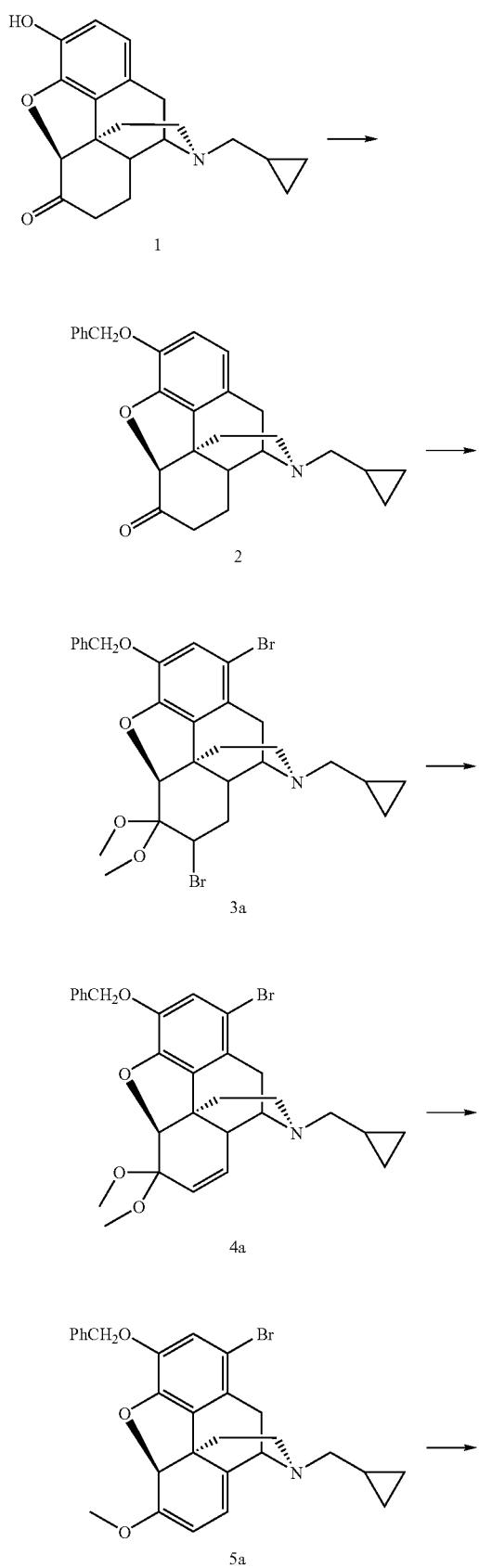

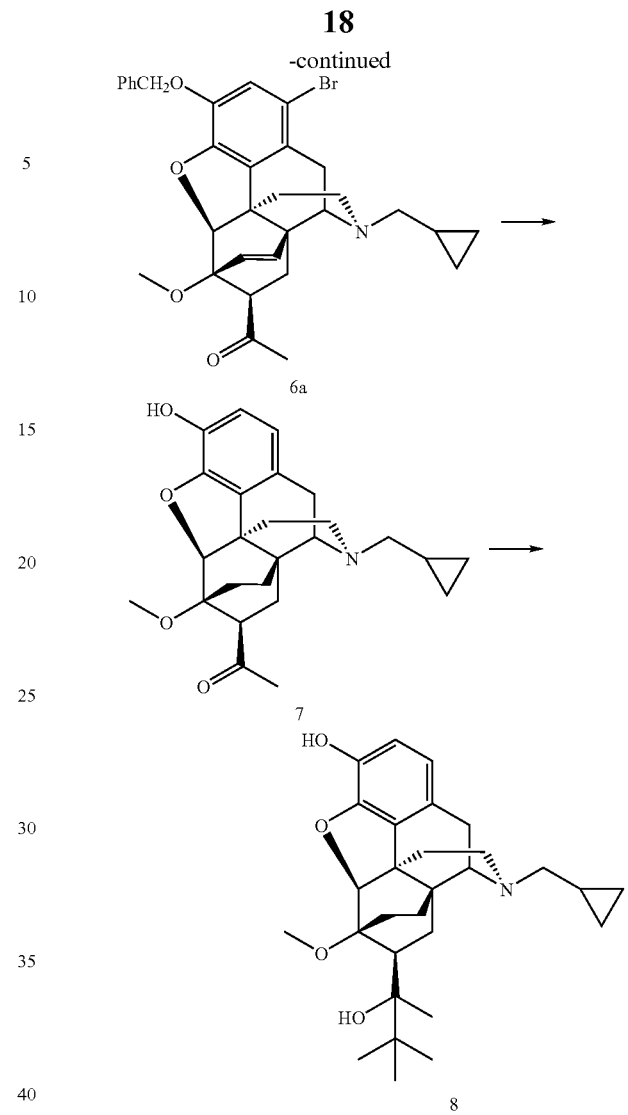

Synthesis of Compound 7 from Compound 1—Process 1:
In one iteration according to reaction scheme 2a, compound 7 was prepared as follows:
(a) Synthesis of Compound 2
To the compound 1 (3-hydroxyl-N-cyclopropanemethyl-norhydromorphone, 5.1 g, 0.0157 mole, 1.0 eqv) and powdered potassium carbonate (8.03 g, 0.0581 mole, 3.7 eqv) in 125 mL wet DMF (containing 5% water) under nitrogen was added benzyl bromide (2.2 mL, 0.0185 mole, 1.18 eqv); the resulting mixture was stirred at room temperature. The reaction was monitored with HPLC. After three hours, to the reaction was added 500 mL ethyl acetate, the mixture was washed with brine (3×100 mL); the organic phase was then dried over anhydrous sodium sulfate. After filtering, the volatiles of filtrate were removed. It gave sticky brown oil. The residue was further purified on silica gel column with 4:1 EtOAc/DCM+1% MeOH+1% Et$_3$N; it gave 7.6 g sticky oil with purity=86%. Yield=100%.
(b) Synthesis of Compound 2a
To the solution of intermediate 2 (5.7 g, 0.0124 mole, one eqv) and dry DMF (66 mL) was added sodium hydride in 60% mineral oil (0.74 g, 0.0186 mole, 1.5 eqv). The resulting light yellow mixture was stirring under nitrogen for 15 min and then cooled to 0° C. in ice bath for 10 minutes, dimethyl sulfate (2.07 mL, 0.0174 mole, 1.4 eqv) was then added to the cooled light yellow mixture and stirred for 30 min. The reaction was poured into ice/water mixture (250 mL) and the product was extracted with ethyl acetate (400 mL); the organic phase was separated and washed with 1% ammonium hydroxide brine (50 mL×5 ), and dried over anhydrous sodium sulfate. After removing the volatiles, a oil residue was left. The crude material was purified on silica gel with 3:1:1 EtOAc/Heptane/DCM+1% Et$_3$N+1% MeOH. The final product was obtained as glass liquid, 2.8 g, purity=90%, yield=53%. HNMR confirmed the desired structure.

(c) Synthesis of Compound 3

To the cooled solution of intermediate 2a (1.3 g, 0.0028 mole, 1.0 equiv) in 20 ml methanol in ice bath (cooled 10 min in advance) was added a cold solution of MeSO$_3$H (1.3 mL, 0.0142 mole, 5 eqv) in MeOH (13 mL, 0° C.); The resulting solution was stirred at 0° C. for 15 min. N-bromoacetamide (0.95 g, 0.0068 mole, 5 eqv) 2.4 eqv) was added. The reaction was stirred in ice bath for 1.5 hours and was then treated with con. NH$_4$OH (6 mL) and water (15 mL). It was stirred for 15 min. The reaction mixture was filtered. The collected solid was dried in vacuum at room temperature overnight. The product was obtained as white solid, 1.75 g, yield=100% and purity=89%. LC-MS: M+1=620.4.

(d) Synthesis of Compound 4

To the cooled solution of intermediate 3 (1.5 g, 0.0244 mole, 1.0 eqv) in 18 ml NMP in ice bath (cooled 10 min in advance) was added a powdered KOH (1.51 g, 0.027 mole, 11 eqv). Then the ice bath was removed, the reaction temperature was gradually heated to 35° C. (oil bath temperature) and stirred at 30° C. for 3 hr; HPLC examination indicated the reaction was done. The reaction was cooled in ice bath; 70 mL de-gassed water was added, the product was extracted with toluene (3×40 mL), the combined organic phases were washed with water (2×60 mL and dried over anhydrous sodium sulfate.

After removing the volatiles, it gave a light yellow oil 1.3 g, yield=99%, purity=95%. LC-MS: M+1=538.4

(e) Synthesis of Compound 5

To the cooled solution of starting material 4 (1.3 g, 2.44 mmole, 1.0 eqv) in 10 ml chloroform in ice bath (cooled 10 min in advance) was added a chlorotrimethylsilane (1.3 mL, 10.2 mmol, 4.2 eqv). After stirring at room temperature for 15 min, 0.3 mL of MeSO$_3$H (3.28 mmol, 1.34 eqv) was added dropwise. The reaction was then stirred at room temperature for 15 min, then warmed to 35° C. (oil bath) for 45 min, then another 0.18 mL MeSO$_3$H was added. The reaction was kept stirring at 35° C. for another two hrs. After cooling to room temperature, the reaction was poured into 60 mL ice cold 5% ammonium hydroxide solution. The organic phase was separated. The aqueous phase was extracted with dichloromethane (3×40 mL). The combined organic extracts were washed with water (3×50 mL) and dried over anhydrous sodium sulfate. After removing the volatiles, it gave sticky oil, 1.0 g with purity=69%. LC-MS: M+1=506.4.

(f) Synthesis of Compound 6

To the solution of starting material 5 (0.5 g, 1 mmole, 1.0 eqv) in toluene (6 mL) was methyl vinyl ketone (2.2 mL, 27 mmol, 27 eqv) was added. The resulting reaction solution was heated at 75° C. (oil bath temperature) for 30 h, then at room temperature over the weekend. After removing the volatiles, it left 0.62 g light brown sticky oil that contained the desired product. LC-MS: M+1=576.17.

(g) Synthesis of Compound 7

The solution of intermediate 6 (0.3 g, 0.5 mmol ) in 15 mL methanol was hydrogenised under 60 spi H$_2$ in the presence of Pd/C catalyst at 60° C. (oil bath) for two hrs. After cooling to room temperature, the solid was filtered. The filtrate was evaporate to a light brown solid that contained the desired product. LC-MS: M+1=410.4.

Synthesis of Compound 7 from Compound 1—Process 2:

In another iteration according to reaction scheme 2a, compound 7 was prepared as follows:

(a) Synthesis of Compound 3 Directly from Compound 2

The intermediate 2 (2.5 g), methanol (5 mL), CH(OMe)$_3$ (1 mL), CHCl$_3$ (13 mL) and MeSO$_3$H (1 g) were heated at 50° C. for 1 h. A solution of Br$_2$ (1.9 g) in CHCl$_3$ (10 mL) was added dropwise over 15 min at 50° C. It was stirred for 30 min and then added to a solution of c-NH$_4$OH (3 mL) in water (20 mL). It was work up in CHCl$_3$-water. The organic layer was pumped down to dryness, re-dissolved in toluene, pumped down to dryness again to give the product as a stick solid.

(b) Synthesis of Compound 3a

The starting material (2.3 g) was dissolved in MeOH (13 mL) and cool to 0° C. A cold solution of MeSO$_3$H (0.5 g) in MeOH (10 mL, 0° C.) was added. It was stirred at 0° C. for 15 min. NBA (0.73 g) was added. It was stirred at 0° C. for 30 min and treated with c-NH$_4$OH (5 mL) and water (50 mL). The aqueous layer was separated and extracted with chloroform (2×20 mL). The combined organic layers were washed with water (2×25 mL), pumped down to dryness to give 2.1 g of the product as a sticky solid.

(c) Synthesis of Compound 4a and Compound 5a

The compound of 3a (0.7 g) was dissolved in DMSO (10 mL). KOBu-t (1 g) was added. It was stirred at rt for 1 h to form 3-benzyl-6,6-dimethoxy-7-bromo-N-cyclopropanemethyl-normorphinone 4a. It was then heated at 50° C. for 4 h and was cooled down to rt. Water (50 mL) and Toluene 20 mL was added. The aqueous layer was separated and extracted with toluene (20 mL). The combined organic layers were washed with water (2×25 mL), pumped down to dryness to give 0.6 g of 3-benzyl-N-cyclopropanemethyl-nororipavine 5a as a sticky solids (0.5 g).

(d) Synthesis of Compound 6a

The compound 5a (0.5 g) was dissolved in toluene (5 mL). Methyl vinyl ketone (1.5) was added. It was heated at 60° C. for 20 h. It was cooled down to rt, diluted with water (30 mL), extracted with chloroform (2×20 mL). The organic layer was pumped down to dryness, re-dissolved in IPA, and pumped down again to give the product as a sticky material (0.5 g).

(e) Synthesis of Compound 7

The compound 6a (0.5 g) was dissolved methanol (5 mL). 5% Pd on carbon (0.1 g) was added. The flask was vacuumed/hydrogen-filling three times. It was heated and stirred under hydrogen pressure (50 PSI) at 45° F. for 18 h. The reaction was completed as shown by HPLC. It was filtered. The carbon cake was washed with MeOH (2×5). It was pumped down to dryness. The solid obtained was re-dissolved in THF and pumped down to dryness to give the product as a solid, 0.35 g.

Synthesis of Compound 8

Irrespective of the route by which compound 7 is prepared, compound 8 was synthesized from compound 7 in accordance with the following procedure. A solution t-BuLil (1.7 M in pentane, 2 mL) were added to a flask under nitrogen and keep at rt. A solution of compound 7 (0.14 g) in toluene (5 mL) was added. It was stirred at rt for 2 h, quenched with water (10 mL). The pH was adjusted with HOAc and c-NH$_4$OH to pH=9. The mixture was extracted with chloroform (2×20 mL). The organic layer was back washed with water (10 mL), pumped down to dryness, re-dissolved in IPA, and pumped down again to give the product as a solid, 0.1 g.

What is claimed is:

1. A process for the preparation of compound 8 according to the following reaction scheme:

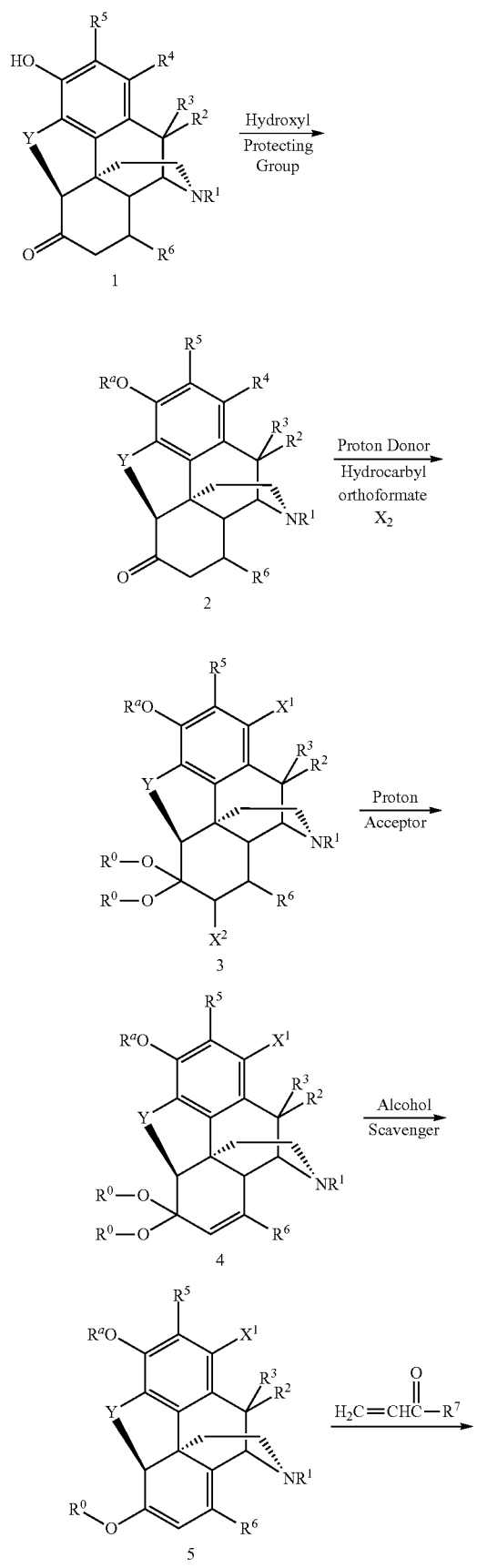
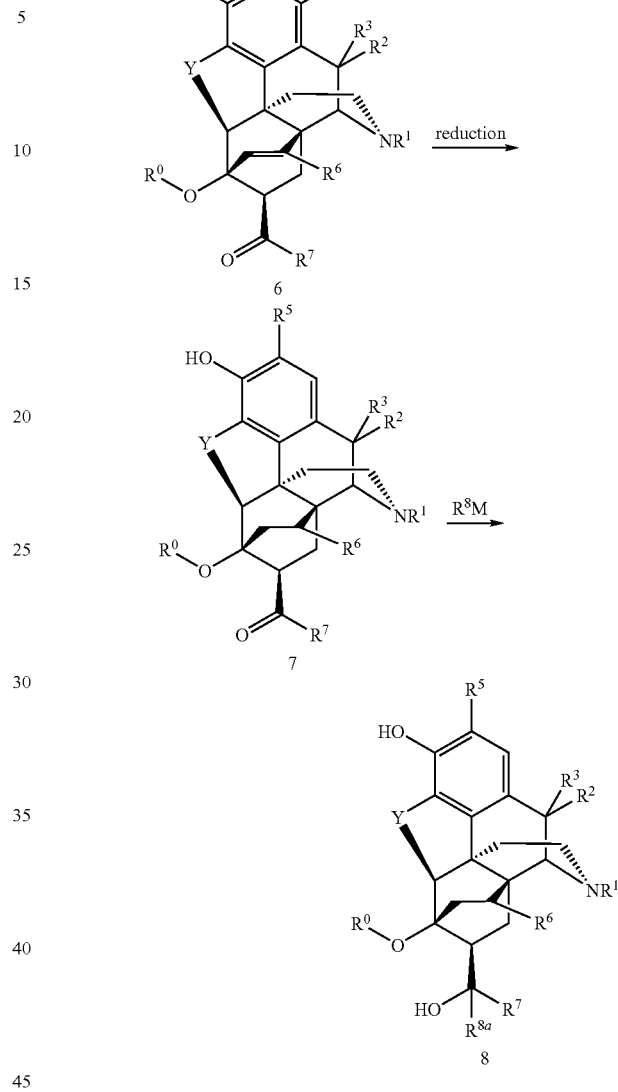

wherein:
R⁰ and R⁸ are independently selected from the group consisting of hydrocarbyl, and substituted hydrocarbyl;
R¹, R⁷ and R⁸ᵃ are independently selected from the group consisting of hydrogen, hydrocarbyl, and substituted hydrocarbyl;
R², R³, R⁴, R⁵, and R⁶ are independently selected from the group consisting of hydrogen, halogen, ORᵇ, hydrocarbyl, and substituted hydrocarbyl, or R² and R³ may together form {-}=O;
Rᵃ is a hydroxyl protecting group;
Rᵇ is selected from the group consisting of hydrogen, hydrocarbyl, and substituted hydrocarbyl;
M is selected from Group IA metal salts, and Group IIA metal salts;
X, and X² are independently selected from the group consisting of bromide, and chloride;
X¹ is bromide or chloride when R⁴ is hydrogen, and X¹ is R⁴ when R⁴ is not hydrogen; and
Y is selected from the group consisting of oxygen, sulfur, and nitrogen.

2. The process of claim 1, wherein:
$R^1$, $R^7$ and $R^{8a}$ are independently selected from the group consisting of hydrogen alkyl, substituted alkyl, alkenyl, substituted alkenyl, aryl, and substituted aryl;
M is selected from the group consisting of NaR, LiR, or $RMgX^3$, where $X^3$ is chloride or bromide and R is a hydrocarbyl or substituted hydrocarbyl;
X, $X^1$, and $X^2$ are each bromide; and
Y is oxygen.

3. The process of claim 1, wherein
$R^1$ is {–}$CH_2$-cyclopropyl;
$R^2$, $R^3$, $R^5$, and $R^6$ are each hydrogen;
$R^7$ is methyl;
$R^8$ is tertiary butyl; and
Y is oxygen.

4. The process of claim 1, wherein the molar ratio of compound 1 to oxygen protecting group is from about 1:1 to about 1:3, the reaction is conducted in the presence of a solvent selected from the group consisting of an organic solvent, a protic solvent, an aprotic solvent, and combinations thereof, and the reaction is conducted at a temperature ranging from about 20° C. to about 50° C.

5. The process of claim 4, wherein the oxygen protecting group is selected from the group consisting of aryl-$CH_2$Br.

6. The process of claim 1, wherein the molar ratio of compound 2 to hydrocarbyl orthoformate to proton donor is from about 1:1:1.5 to about 1:2:3, the reaction is conducted in the presence of an aprotic solvent, and the reaction is conducted at a temperature ranging from about 20° C. to about 120° C.

7. The process of claim 6, wherein the hydrocarbyl orthofomate is selected from the group consisting of trimethyl orthoformate, and triethyl orthoformate, and the proton donor is selected from the group consisting of $MeSO_3H$, poly $H_3PO_4$, $H_3PO_4$, $H_2SO_4$, HCl, HBr, $HClO_4$, HI, $HNO_3$, $CF_3SO_3H$, p-methyltoluenesulfonic acid, $HClO_3$, $HBrO_4$, $HIO_3$, and $HIO_4$.

8. The process of claim 6, wherein the reaction is conducted in the presence of an alcohol-containing solvent.

9. The process of claim 8, wherein X is bromine added in an amount ranging from about 2 to about 2.5 equivalents for each equivalent of compound 2.

10. The process of claim 1, wherein the molar ratio of compound 3 to proton acceptor is from about 1:1 to about 1:10, the reaction is conducted in the presence of an aprotic solvent, and the reaction is conducted at a temperature ranging from about 40° C. to about 120° C.

11. The process of claim 10, wherein the proton acceptor is selected from the group consisting of hydroxide salts.

12. The process of claim 1, wherein the molar ratio of compound 4 to alcohol scavenger is from about 1:0.3 to about 1:3, the reaction is conducted in the presence of an aprotic solvent, and the reaction is conducted at a temperature ranging from about 0° C. to about 80° C.

13. The process of claim 12, wherein the alcohol scavenger is a methanol scavenger selected from the group consisting of $P_2O_5$, $POCl_3$, $POBr_3$, $PCl_3$, $PBr_3$, $SOCl_2$, $SOBr_2$, $MeSO_2Cl$, $(MeSO_2)_2O$, $SO_3$, $(CF_3SO_2)_2O$, $(CF_3CO)_2O$, and $(CR_3CO)_2O$, wherein R is an alkyl group.

14. The process of claim 1, wherein the molar ratio of compound 5 to

is from about 1:1 to about 1:10, the reaction is conducted in the presence of an organic solvent, and the reaction is conducted at a temperature ranging from about 20° C. to about 120°.

15. The process of claim 14, wherein $R^7$ is a methyl group.

16. The process of claim 1, wherein the reduction is catalytic reduction, the molar ratio of compound 6 to catalyst is from about 1:0.0005 to about 1:0.05, the reaction is conducted in the presence of an organic solvent, the reaction is conducted under pressurized hydrogen, and the reaction is conducted at a temperature ranging from about 20° C. to about 120° C.

17. The process of claim 16, wherein the catalyst is a transition metal catalyst selected from the group consisting of Pd/C, Pt/C, Ru/C, and Rh/C; and the hydrogen pressure is between about 0 and about 500 PSI.

18. The process of claim 1, wherein the molar ratio of compound 7 to $R^8M$ is from about 1:2 to about 1:10, the reaction is conducted in the presence of an aprotic solvent, and the reaction is conducted at a temperature ranging from about 60° C. to about 120° C.

19. The process of claim 18, wherein $R^8$ is tertiary butyl.

20. The process of claim 19, wherein M is MgCl.

21. The process of claim 1, wherein the yield of compound 8 is from about 8% to about 20%; and the purity of compound 8 is at least 98% as determined by chromatography.

22. The process of claim 1, wherein the configuration of carbons 5, 13, 14, and 9, respectively, of any of compounds 1 to 8 is selected from the group consisting RRRS, RRSS, SRRS, SRSS, RSRR, RSSR, SSRR, and SSSR, provided that the C15 and the C16 atoms are both either on the alpha face of the molecule or the beta face of the molecule.

* * * * *